United States Patent [19]

Smith et al.

[11] Patent Number: 5,077,293

[45] Date of Patent: Dec. 31, 1991

[54] 1-INDOLYALKYL-4-(ALKOXYPYRIMIDINYL)PIPERAZINES

[75] Inventors: David W. Smith, Clinton; Frank D. Yocca, Madison; Joseph P. Yevich, Southington; Ronald J. Mattson, Meriden, all of Conn.

[73] Assignee: Bristol-Myers Squibb Co., New York, N.Y.

[21] Appl. No.: 546,121

[22] Filed: Jun. 29, 1990

[51] Int. Cl.$^5$ .................. A61K 31/505; C07D 403/00
[52] U.S. Cl. ...................................... 514/253; 544/295
[58] Field of Search .................. 544/295; 514/253

[56] References Cited

U.S. PATENT DOCUMENTS

| | | | |
|---|---|---|---|
| 3,146,234 | 8/1964 | Archer | 544/295 X |
| 3,188,313 | 6/1965 | Archer | 544/360 X |
| 3,562,278 | 2/1971 | Archer | 544/360 X |
| 4,954,502 | 9/1990 | Smith et al. | 514/253 |

FOREIGN PATENT DOCUMENTS

| | | |
|---|---|---|
| 354094 | 2/1990 | European Pat. Off. |
| 2124210 | 2/1984 | United Kingdom |
| 2162522 | 2/1986 | United Kingdom |

OTHER PUBLICATIONS

Fuller, "Pharmacologic Modification . . . ", J. Clin. Psychiatry, 47:4 (Suppl.) Ap. 1986, pp. 4–8.
S. J. Enna, editor, *Antidepressants* 1981 Raven Press, New York, pp. 1–12.
Johnson et al., J. Org. Chem. 25, 569 (1969).
Skolnick et al., Br. J. Pharm. (1985), 86, p. 637.
Schatzberg et al., J. Clin. Psychopharm. 7/6 Suppl. 1987, pp. 445–495.

*Primary Examiner*—Catherine S. Kilby Scalzo
*Attorney, Agent, or Firm*—Richard P. Ryan

[57] ABSTRACT

Certain 1-indolylalkyl-4-(alkoxypyrimidinyl)piperazines of Formula I are useful antidepressant agents. The

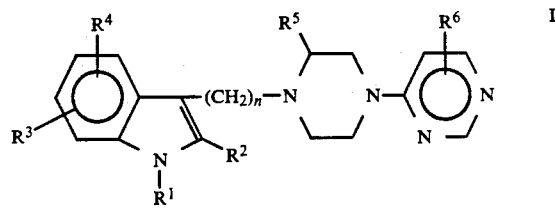

substituents $R^1$, $R^2$ and $R^5$ are hydrogen or lower alkyl; $R^3$ and $R^4$ are hydrogen, alkyl, alkoxy, alkythio, carboxamido, halo, or trifluoromethyl; $R^6$ is alkoxy; and n is the integer 2 or 3.

21 Claims, No Drawings

1-INDOLYALKYL-4-(ALKOXYPYRIMIDINYL)PIPERAZINES

BACKGROUND OF THE INVENTION

This invention generally pertains to heterocyclic carbon compounds having drug and bio-affecting properties and to their preparation and use. In particular the invention is concerned with 1,4-disubstituted piperazine derivatives wherein one substituent is indol-3-yl-alkyl and the other is a substituted pyrimidin-4-yl moiety. These compounds possess a unique serotonergic profile that should make them useful in treatment of depression.

Archer disclosed a large series of CNS-depressant indolylalkylpiperazines in U.S. Pat. No. 3,188,313. Among a large number of possible substituents on the 4-nitrogen atom of the piperazine ring was pyrimidine (unsubstituted). In U.S. Pat. No. 3,562,278, Archer disclosed and claimed a series of 1-indolyl-ethyl-4-substituted-piperazines. Among the possible 4-substituents listed is 2-pyrimidinyl, again unsubstituted. The pharmacologic action disclosed for these art compounds is general CNS and psychomotor depression—in direct opposition to the antidepressant effects of the novel compounds of the instant invention.

SUMMARY AND DETAILED DESCRIPTION OF THE INVENTION

In its broadest aspect, the present invention is concerned with piperazinyl derivatives having useful antidepressant properties characterized by a compound of Formula I.

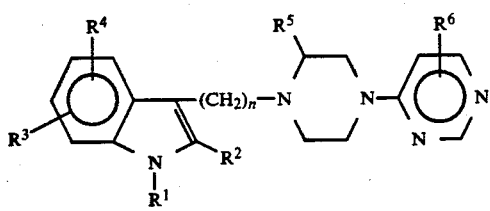

In Formula I; $R^1$ is selected from hydrogen, lower alkyl, and aryl-lower alkyl, e.g. benzyl. The descriptive term "lower" is used herein to denote an organic radical containing from 1 to 4 carbon atoms. Aryl means phenyl or $R^3$-substituted phenyl. $R^2$ and $R^5$ are independently selected from hydrogen and lower alkyl. $R^3$ and $R^4$ are independently selected from among hydrogen, lower alkyl, lower alkoxy, lower alkylthio, carboxamide, halogen and trifluoromethyl. $R^6$ is lower alkoxy and n is the integer 2 or 3. Preferred classes of compounds are those wherein $R^3$ is 5-fluoro- and wherein $R^5$ is 5-methoxy.

Additionally compounds of Formula I also encompass all pharmaceutically acceptable acid addition salts and/or solvates thereof. The present invention is also considered to include stereoisomers as well as optical isomers, e.g. mixtures of enantiomers as well as individual enantiomers and diasteromers, which arise as a consequence of structural asymmetry in certain compounds of the instant series. Separation of the individual isomers is accomplished by application of various methods which are well known to practitioners in the art.

It is to be understood that, as used herein, halogen denotes fluorine, chlorine, bromine and iodine; with the term "lower alkyl" referring to both straight and branched chain carbon radicals of from to 4 carbon atoms inclusive. Illustrative of these radicals are carbon chains which can be methyl, ethyl, propyl, isopropy, 1-butyl, 1-methylpropyl and 2-methylpropyl. Carboxamide intends a

radical.

The pharmaceutically acceptable acid addition salts of the invention are those in which the counter-ion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of a Formula I base with the selected acid preferably by contact in solution employing an excess of commonly used inert solvents such as water, ether, benzene, methanol, ethanol, ethyl acetate and acetonitrile. The may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic, and others.

The compounds of Formula I can be prepared by means of the processes shown in Scheme 1.

Scheme 1

Scheme 1

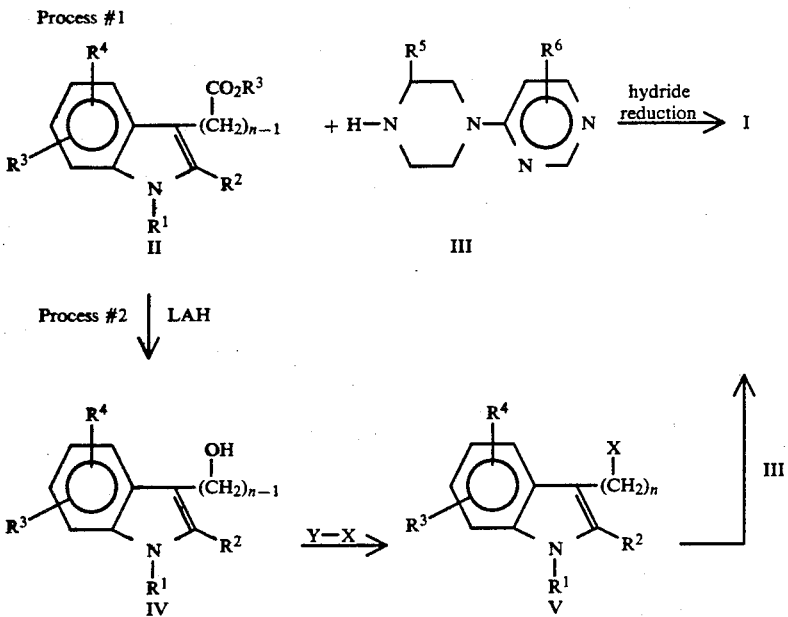

For the two processes of Schemes 1, $R^1$ through $R^6$ and n are as defined hereinabove. The reagent Y-X represents an organic leaving group reagent wherein X is the leaving group fragment such as tosyl, mesyl, halide, sulfate, phosphate and so forth; and Y is either a proton or a counter ion; e.g. Y-X can be HBr or tosyl chloride and the like. "Hydride reduction" concerns intended reductive amination of compound II by III, particularly the reduction of the initial complex of compound II and III to provide product I. Preferred reagents for this use in Process #1 are $B_2H_6$ and LAH or an equivalent. The reagents of Scheme I and their acronyms are familiar to the practitioner skilled in organic synthesis and their structure and usage would be readily understood.

Process #1 in Scheme I comprises the combination of an indole carboxylic acid or ester of formula II with a pyrimidinylpiperazine intermediate of formula III followed by treatment with diborane, lithium aluminum hydride or an equivalent to give the product of formula I.

Process #2 comprises reduction of the indole intermediate of formula II to the corresponding alcohol of formula VI which is converted to an activated intermediate of formula V in which the alcoholic moiety is now an organic leaving group. Reaction of intermediate V with a pyrimidinylpiperazine of formula II then provides product I.

Reagents, solvents, and reaction conditions for the above described steps of the two processes would be known to one skilled in organic synthesis as all the steps comprise standard organic reactions, the details of which are readily available in the chemical literature. These processes may be adapted to variation in order to produce other compounds embraced by this invention but not specifically disclosed. Variations of the methods to produce the same compounds in somewhat different fashion will also be evident to one skilled in the art.

To provide greater descriptive detail, representative synthetic examples are provided hereinbelow in the "Description of Specific Embodiments" section. Similarly, preparations of reaction starting materials and intermediates, while readily available in the chemical literature, are also described using specific examples in that section of the paten specification.

The compounds comprising the present invention inhibit the re-uptake of endogenous serotonin. Selective inhibitors of serotonin uptake are effective for the treatment of mental depression and have been reported to be useful for treating chronic pain (see: R. W. Fuller, "Pharmacologic Modification of Serotonergic Function: Drugs for the Study and Treatment of Psychiatric and Other Disorders", *J. Clin. Psychiatry* 47:4 (Suppl.) April 1986, pp. 4-8). Compounds of the present invention are also envisioned to be useful in the following disorders: obsessive-compulsive disorder, feeding disorders, anxiety disorders and panic disorders.

Additionally, selected compounds of the invention potently inhibit norepinephrine re-uptake and blockade of endogenous norepinephrine re-uptake is also a mechanism through which it is believed that various antidepressant agents exert their therapeutic effect (see: "Antidepressants: Neurochemical, Behavioral, and Clinical Perspectives", edited by S. J. Enna, J. B. Malick and E. Richardson, (1981), Raven Press, New York, pp. 1-12).

Determination of endogenous monoaminergic re-uptake inhibition values both for serotonin and norepinephrine was accomplished using test methods described by P. Skolnick, et al., *Br. J. Pharmacology* (1985), 86, pp. 637-644; with only minor modifications. In vitro $IC_{50}$ (nM) test values were determined for representative compounds of Formula I based on their inhibition of synaptosomal reuptake of tritiated serotonin. Test data $IC_{50}$ values lower than 500 nM are considered to reflect activity as an inhibitor of serotonin reuptake. Compounds with $Ic_{50}$ values lower than 100 nM comprise preferred compounds.

Another aspect of the instant invention provides a method for treating a mammal afflicted with depression or chronic pain which comprises administering systemically to said mammal a therapeutically effective amount of a compound of Formula I or a pharmaceutically acceptable acid addition salt thereof.

The administration and dosage regimen of compounds of Formula I is considered to be done in the same manner as for the reference compound fluoxetine, cf: Schatzberg, et al., *J. Clin. Psychopharmacology* 7/6 Suppl. (1987) pp. 4451-4495, and references therein. Although the dosage and dosage regimen must in each case be carefully adjusted, utilizing sound professional judgment and considering the age, weight and condition of the recipient, the route of administration and the nature and gravity of the illness, generally the daily dose will be from about 0.05 to about 10 mg/kg, preferably 0.1 to 2 mg/kg, when administered parenterally and from about 1 to about 50 mg/kg, preferably about 5 to 20 mg/kg, when administered orally. In some instances, a sufficient therapeutic effect can be obtained at lower doses while in others, larger doses will be required. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a similar quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets o capsules and may contain conventional excipients such as binding agents (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

DESCRIPTION OF SPECIFIC EMBODIMENTS

The compounds which constitute this invention, their methods of preparation and their biologic actions will appear more fully from consideration of the following examples, which are given for the purpose of illustration only and are not be construed as limiting the invention in sphere or scope. In the following examples, used to illustrate the foregoing synthetic processes, temperatures are expressed in degrees Celsius and melting points are uncorrected. The nuclear magnetic resonances (NMR) spectral characteristics refer to Chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported a broad singlet (bs), singlet (s), multiplet (m) or doublet (d). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

The following examples describe in detail the preparation of compounds of Formula I, as well as synthetic intermediates in each process. It will be apparent to those skilled in the art that modifications, both of materials and methods, will allow preparation of other compounds disclosed herein. From the foregoing description and the following examples it is believed that one skilled in the art is able to use the invention to the fullest extent.

A. Preparation of Intermediate Compounds

Some representative procedures for preparation of synthetic intermediate compounds utilized in the three processes of Scheme 1 are given hereinbelow. Most starting materials and certain intermediates (e.g. Formula II and V compounds), are either commercially available or procedures for their synthesis are readily available in the chemical literature allowing their full utilization by one skilled in the art of organic synthetic chemistry.

COMPOUNDS OF FORMULA II

Example 1

General Method: 5-Fluoroindole-3-propionic acid

A modification of a procedure reported by Johnson[1] for the preparation of indole-3-propionic acid was used.
[1]H. E. Johnson and D. G. Crosby, *J. Org. Chem.*, 25, 569(1969).

Thus, a solution of 5-fluoroindole (1.35 g, 0.010 mole) in 10 mL of acetic acid containing acrylic acid (1.5 mL, 0.022 mole) and acetic anhydride (1.9 mL, 0.02 mole) was heated (oil bath) at 90° C. under Ar for 5 days. The volatiles were then removed in vacuo and the residue was taken up in 3 N NaOH. Insoluble material was removed by filtration and the filtrate was acidified with conc. HCl and then extracted with CH$_2$Cl$_2$. The organic extract was dried (Na$_2$SO$_4$) and evaporated to give the product (1.19 g, 57%) as a solid which was used without further purification: IR (neat) 3420, 1710 cm$^{-1}$; $^1$Hnmr (200 MHz, CDCl$_3$) $\delta$ 7.94 (br s, 1H), 7.28-7.18 (m, 3H), 7.05 (d, J=2.5 Hz, 1H), 6.93 (dt, J=9.0, 2.6 Hz, 1H), 3.05 (t, J=7.5 Hz, 2H), 2.73 (t, J=7.6 Hz, 2H).

By appropriate modification of the general method, other Formula II compounds are readily obtainable.

Example 2

5-Chloroindole-3-propionic acid

The crude product was chromatographed (SiO$_2$/5-20% ethyl acetate-CH$_2$Cl$_2$) to give the title compound as a beige solid, m.p. 100°-102° C.: Yield=41%; IR (neat) 3435, 1695 cm$^{-1}$; hu 1Hnmr (200 MHz, CDCl$_3$) $\delta$ 8.00 (br s, 1H), 7.56 (d, J=1.8 Hz, 1H), 7.27 (d, J=8.7 Hz, 1H), 7.15 (dd, J=8.6, 1.9 Hz, 1H), 7.05 (d, J=2.3 Hz, 1H), 3.07 (t, J=7.5 Hz, 2H), 2.75 (t, J=7.4 Hz, 2H).

Example 3

6-Fluoroindole-3-propionic acid

The crude product was chromatographed (SiO$_2$/20% hexane-ethyl acetate) to give the title compound as a beige solid, m.p. 98°-102° C.: Yield=23%, IR (neat) 3400, 1687 cm$^{-1}$; $^1$Hnmr (200 MHz, CDCl$_3$) δ 7.97 (br s, 1H), 7.50 (dd, J=8.7, 5.4 Hz, 1H), 7.07-6.99 (m, 2H), 6.89 (dt, J=9.5, 2.2 Hz, 1H), 3.09 (t, J=7.5 Hz, 2H), 2.76 (t, J=7.4 Hz, 2H).

Example 4

1-Ethylindole-3-propionic acid

The title compound was prepared from 1-ethylindole according to the general procedure to give a brown solid, m.p. 50° C.: Yield=76%; IR (neat) 1710 cm$^{-1}$; $^1$Hnmr (200 MHz, CDCl$_3$) δ 7.62-7.57 (m, 1H), 7.35-7.07 (m, 3H), 6.95 (s, 1H), 4.13 (q, J=7.3 Hz, 2H), 3.15-3.08 (m, 2H), 2.81-2.74 (m, 2H), 1.44 (t, J=7.3 Hz, 3H).

Example 5

1-Benzylindole-3-propionic acid

The product was prepared from 1-benzylindole according to the general procedure. The crude material was chromatographed (SiO$_2$/10-30% ethyl acetate-hexane) to give a solid, m.p. 110°-112° C.: Yield=52%; IR (neat) 1695 cm$^{-1}$; $^1$Hnmr (200 MHz, CDCl$_3$) δ 3.13 (t, J=7.6 Hz, 2H), 2.78 (t, J=7.5 Hz, 2H).

Compounds of Formula VI

Example 6

General Method: 5-Fluoro-3-(3-hydroxypropyl)indole

To a suspension of LiAlH$_4$ (433 mg, 11.4 mmol) in 20 mL of dry tetrahydrofuran at 5°-10° C. under Ar was added a solution of 5-fluoroindole-3-propionic acid (1.179 g, 5.7 mmol) in 5 mL of tetrahydrofuran. After 10 min the cooling bath was removed and the mixture was stirred at room temperature for 30 min and finally it was heated to reflux for 30 min. The resulting gummy mixture was allowed to cool to room temperature and then the reaction was quenched by the sequential addition of 0.5 mL of H$_2$O, 0.5 mL of 15% NaOH solution and finally 1.5 mL of H$_2$O. The mixture was then diluted with ethyl acetate, dried (MgSO$_4$) and evaporated to give a yellow-green oil. Flash chromatography (SiO$_2$/CH$_2$Cl$_2$-ethyl acetate=2:1) afforded the product (918 mg, 83%) as an oil: IR (neat) 3420, 1583 cm$^{-1}$; $^1$Hnmr (200 MHz, CDCl$_3$) δ 7.94 (br s, 1H), 7.28-7.20 (m, 2H), 7.03 (d, J=2.4 Hz, 1H), 6.92 (dt, J=9.1, 2.5 Hz, 1H), 3.71 (t, J=6.4 Hz, 2H), 2.80 (t, J=7.5 Hz, 2H), 2.02-1.88 (m, 2H), 1.33 (br s, 1H).

Example 7

5-Chloro-3-(3-hydroxypropyl)indole

The title compound was prepared according to the general procedure to give a light brown oil which was used without further purification: Yield=96%; IR (neat) 3430, 3300, 1462 cm$^{-1}$.

Example 8

6-Fluoro-3-(3-hydroxypropyl)indole

The product was prepared according to the general procedure, except that the reaction was run at room temperature for 5 h. Standard work-up gave the title compound as a light brown gum: Yield=90%; IR (neat) 3420, 1630 cm$^{-1}$.

Example 9

1-Ethyl-3-(3-hydroxypropyl)indole

The reaction was done at room temperature for 18 h, according to the general procedure. The title compound was obtained as a light brown oil: Yield=90%; IR (neat) 3360 cm$^{-1}$.

Example 10

1-Benzyl-3-(3-hydroxypropyl)indole

The reaction was done as in the previous example to give the title compound as a solid, m.p. 75° C.: Yield=100%; IR (neat) 3340 cm$^{-1}$.

Example 11

2-Methyl-3-(3-hydroxypropyl)indole

The reaction was done as described in the general procedure, except that it was quenched after stirring for 1 h at room temperature. Standard work-up gave a gum which was chromatographed (SiO$_2$/CH$_2$Cl$_2$-ethyl acetate=2:1) to give the title compound as a syrup: Yield=59%; IR (neat) 3540, 3400 cm$^{-1}$.

Example 12

3-(2-hydroxyethyl)-1H-indole

To a stirred suspension of LiAlH$_4$ (3.24 g) in THF (200 mL) at 0° C. and under N$_2$ atmosphere was added dropwise a THF solution (50 mL) containing indole-3-acetic acid (10.0 g). After the addition was complete, the reaction was heated at reflux for 3 h, after which time the mixture was cooled to 0° C. and water (3.3 mL) added, followed by 15% NaOH (3.3 mL), and finally additional water (9.9 mL). The reaction was filtered and the filter cake washed with Et$_2$O. The organic layers were combined, dried with anhydrous MgSO$_4$, filtered, and concentrated under reduced pressure to yield 3-(2-hydroxyethyl)indole (VI; 7.4 g; 80%).

Example 13

5-Fluoro-3-(2-hydroxyethyl)indole

To a suspension of LiAlH$_4$ (8.60 g, 0.23 mole) in 400 mL of dry THF was added 5-fluoro-3-indoleglyoxylic acid ethyl ester (13.50 g, 0.057 mole) portionwise at room temperature. Preparation of this ester intermediate is given hereinbelow. The mixture was heated to reflux under Ar for 1 h and was then cooled at 0° C. and quenched according to the method of Fieser (Fieser and Fieser, "Reagents for Organic Synthesis", Vol. 1, pg. 584). The resulting slurry was filtered and the filter cake was washed with THF. The filtrate was dried (Na$_2$SO$_4$) and evaporated to give the product (10.00 g, 100%) as a yellow oil. It was used as such without further purification; IR (neat) 3420 cm$^{-1}$. $^1$Hnmr (80 MHz, CDCl$_3$). δ: 7.73 (br s, 1H), 7.1-6.4 (m, 4H), 3.57 (t, J=8 Hz, 2H), 2.66 (t, J=8 Hz, 2H), 1.20 (br s, 1H).

5-fluoro-3-indoleglyoxylic acid ethyl ester

To a solution of 5-fluoroindole (7.35 g, 0.054 mole) in 75 mL of anhydrous ether was added oxalyl chloride (5.60 mL, 0.064 mole) dropwise at 0° C. under Ar.

The yellow suspension was stirred at 0° C. for 1½ h and then the solid was collected by filtration and dried in vacuo to give 5-fluoro-3-indoleglyoxylyl chloride (12.0 g, 100%) as a yellow solid; IR (neat) 1765, 1627 cm$^{-1}$.

Compounds of Formula V

Example 14

General Method:
5-Fluoro-3-(3-p-toluenesulfonyloxypropyl)indole

To a solution of 5-fluoro-3-(3-hydroxypropyl)indole (917 mg, 4.75 mmol) in 20 mL of CH$_2$Cl$_2$ at 0° C. under Ar was added triethylamine (728 μL, 5.23 mmol), followed by a solution of p-toluenesulfonyl chloride (994 mg, 5.23 mmol) in 5 mL of CH$_2$Cl$_2$ and then a catalytic amount of 4-dimethylaminopyridine (59 mg, 0.48 mmol). The reaction mixture was stirred at 0° C. for 30 min and then at room temperature for 1½ h. Evaporation of the mixture followed by chromatography (SiO$_2$/CH$_2$Cl$_2$) of the residue gave a gum. The gum was taken up in ether and then the solution was diluted with hexane until an oil separated. Addition of a small amount of CH$_2$Cl$_2$ led to dissolution of the oil and crystallization of the product. Storage at −20° C. and then filtration and drying of the residue in vacuo gave the product (1.378 g, 84%) as fluffy white needles: m.p. 99° C.; IR (CH$_2$Cl$_2$) 3470, 1360, 1178 cm$^{-1}$; $^1$Hnmr (200 MHz, CDCl$_3$) δ 7.90 (br s, 1H), 7.61 (d, J=8.4 Hz, 2H), 7.30 (d, J=8.4 Hz, 2H), 7.27–7.20 (m, 1H), 7.08 (dd, J=9.6, 2.6 Hz, 1H), 6.96–6.94 (m, 1H), 6.88 (dd, J=9.0, 2.5 Hz, 1H), 4.06 (t, J=6.2 Hz, 2H), 2.74 (t, J=7.2 Hz, 2H), 2.42 (s, 3H), 1.99 (dq, J=7.2, 6.2 Hz, 2H).

Example 15

5-Chloro-3-(3-p-toluenesulfonyloxypropyl)indole

The crude product was chromatographed (SiO$_2$/ethyl acetate-hexane=1:1) to give the title compound as a solid, m.p. 80°–83° C.: Yield=80%; IR (neat) 3442, 1350, 1175 cm$^{-1}$.

Example 16

6-Fluoro-3-(3-p-toluenesulfonyloxypropyl)indole

The crude product was chromatographed (SiO$_2$/10–30% ethyl acetate-hexane) to give the title compound as an oil: Yield=84%; IR (neat) 34!0, 1353, 1178 cm$^{-1}$.

Example 17

1-Methyl-3-(3-p-toluenesulfonyloxypropyl)indole

The crude product was triturated with ether and the supernatant was filtered and evaporated to give the title compound as an oil: Yield=83%; IR (neat) 1360, 1175 cm$^{-1}$.

Example 18

1-Ethyl-3-(3-p-toluenesulfonyloxypropyl)indole

The crude product was chromatographed (SiO$_2$/ethyl acetate-hexane=1:1) to give the title compound as an oil: Yield=77%; IR (neat) 1355, 1175 cm$^{-1}$.

Example 19

3-(3-Bromopropyl)-1H-indole

Phosphorus tribromide (17.4 g) in Et$_2$O 30 mL) was added dropwise to a Et$_2$O solution (100 mL) containing 3-(3-hydroxypropyl)indole (VI; 7.5 g) at 0° C. with stirring and under N$_2$ atmosphere. After the addition was complete, the reaction was allowed to warm to 23° C. and continuously stirred for 16 h. At the end of this time, the reaction was cooled to 0° C. and ice (ca. 25 mL) added portionwise and stirred an additional 2 h. The organic phase was separated from the aqueous phase and the aqueous layer extracted with Et$_2$O. The combined organic phases were washed with sat. NaCl solution, dried with MgSO$_4$, filtered, and concentrated under reduced pressure to afford 3-(3-bromopropyl)indole (V; 1.51 g; 15%).

Example 20

5-Fluoro-3-(2-bromoethyl)indole

To a solution of 5-fluoro-3-(2-hydroxyethyl)indole (10.3 g, 0.056 mole) and CBr$_4$ (24.8 g, 0.073 mole) in 100 mL of dry acetonitrile at 0° C. under Ar was added a solution of triphenylphosphine (19.6 g, 0.073 mole) in 200 mL of dry acetonitrile. The mixture was stirred at 0° C. for 1 h and then at room temperature for 2 h. The resulting mixture was evaporated and the residue was chromatographed (SiO$_2$/ethyl acetate-hexane=1:4) to give the product (8.50 g, 61%) as a brown solid; IR (neat) 3440 cm$^{-1}$; $^1$Hnmr (80 MHz, CDCl$_3$) δ: 7.75 (br s, 1H), 7.15–6.57 (m, 4H), 3.53–3.32 (m, 2H), 3.17–2.94 (m, 2H).

COMPOUNDS OF FORMULA II

Example 21

1-(5-Methoxy-4-pyrimidinyl)piperazine—Method 1

To a solution of piperazine (38.40 g, 0.45 mole) in CH$_3$CN (225 mL) was added dropwise a CH$_3$CN (100 mL) solution containing 4-chloro-5-methoxypyrimidine (6.45 g, 0.04 mole) while under nitrogen atmosphere. After the addition was complete the reaction was heated at 60° C. for 0.75 h. The reaction was concentrated under reduced pressure and the residue dissolved in CH$_2$Cl$_2$ and extracted with 5% NaHCO$_3$ and H$_2$O. The organic phase was dried with K$_2$CO$_3$, filtered, and concentrated under reduced pressure. Silica gel chromatography (CH$_2$Cl$_2$: MeOH:NH$_4$—OH; 92:8:0.8) of the concentrate afforded II (7.63 g, 88.1%). Treatment of the base (1.0 g) with ethanolic HCl and crystallization from EtOH/i-PrOH yielded the hydrochloride salt of II (0.50 g, 39.1%, m.p. 207°–211°.

1-(5-Methoxy-4-pyrimidinyl)piperazine—Method 2

A. 4,6-Dihydroxy-5-methoxypyrimidine

A modified procedure of Bretschneider, Richter, and Klötzer, Monatsh. Chem. 96(6), 1661–76 (1965), was used. Absolute methanol (1.0 l) was added with ice bath cooling to sodium methoxide (175 g, 3.24 mole) in a 3 L round bottom flask. When the mixture had cooled to less than 20° C., dimethyl methoxymalonate (162.14 g, 1.00 molc) was added, and then solid formamidine acetate (104.11 g, 1.00 mole) was added. The mixture was stirred in the ice bath for 30 minutes, and then refluxed for 1 hour. The mixture was cooled in a cold water bath and then concentrated HCl (about 350 mL) was added until the mixture was strongly acidic on pH test paper. The precipitate was filtered, suspended in cold water (about 400 ml), and then filtered again. The white powder was dried in vacuo (125.84 g, 88.7%), and carried on without further purification.

B. 4,6-Dichloro-5-methoxypyrimidine

A modified procedure of Bretschneider, Richter, and Klötzer, Monatsh. Chem. 96(6), 1661–76 (1965), was used. A mixture of 4,6-Dihydroxy-5-methoxy-pyrimidine (125.84 g, 0.887 mole), POCl$_3$ (700 mL), and N,N-diethylaniline (50 mL) was refluxed for 3 hours to give a brown solution. The solution was cooled and then the excess POCl$_3$ was removed in vacuo. Hexane (about 300 mL) was added to the residue and the mixture was refluxed with stirring. The hot hexane layer was decanted into a beaker, and residue treated two more times with hot hexane. The hexane extracts (total volume about 1 l) were concentrated in vacuo to give the crude product as a white solid (116.5 g, 73.3%). This material was recrystallized from pet ether to give colorless needles (92.0 g + 16.51 g second crop, 93.1% total recovery).

C. 6-Chloro-5-methoxy-4-(1-piperazinyl)pyrimidine

Piperazine (30 g) was dissolved in water (150 mL) and then solid 4,6-Dichloro-5-methoxypyrimidine (10.00 g, 55.8 mmol) was added. The mixture was vigorously stirred for 2 hr at room temperature during which the 4,6-Dichloro-5-methoxypyrimidine dissolved. The product was extracted from the aqueous reaction mixture with methylene chloride (yield 12.67 g, 99.2%). A sample (5 g) of the crude product was chromatographed on silica gel using a gradient of 20–40% methanol/ethyl acetate as the eluent. The product was then dissolved in acetonitrile and concentrated HCl added to give the salt as a white powder which was dried in vacuo to give the analytical sample (4.0 g, m.p.: 169°–173° C. bubbles).

Anal. Calcd for C$_9$H$_{13}$N$_4$OCl·1.5 HCl·0.2 H$_2$O; C, 37.67; H, 5.24; N, 19.53 H$_2$O; 1.26; Found: C, 37.63; H, 4.99; N, 19.46 H$_2$O; 1.47.

D. 1-(5-Methoxy-4-pyrimidinyl)piperazine

Piperazine (20 g) was dissolved in water (100 mL) in a Parr bottle and then solid 4,6-dichloro-5-methoxypyrimidine (5.00 g, 27.9 mmol) was added. The mixture was vigorously stirred for 2 h at room temperature during which the 4,6-dichloro-5-methoxypyrimidine dissolved. The stirring bar was removed, catalyst (10% Pd/C, 1.0 g) was added to the turbid solution, and the mixture was then hydrogenated (60 psi, 3 h) at room temperature. The catalyst was filtered off and the filtrate extracted 3 times with CH$_2$Cl$_2$. The CH$_2$Cl$_2$ extracts were dried over Na$_2$SO$_4$ and concentrated in vacuo to give a clear oil which solidified upon standing (3.34 g, 61.7%). This crude product was Kügelrohr distilled (yield 3.24 g), dissolved in acetonitrile, and concentrated HCl added to precipitate the product as a white powder which was dried in vacuo (4.32 g, 94.0% from crude product, m.p. 219°–221.5° C.).

Example 22

4-(5-Methoxy-4-pyrimidinyl)-2-methyl-piperazine—Method 1

A mixture of 2-methylpiperazine (27.74 g, 0.28 mole) and 4-chloro-5-methoxy-pyrimidine (8.0 g, 0.06 mole) was heated in a Parr bomb at 100° C. for 1.5 h. The reaction mixture was dissolved in CH$_2$Cl$_2$ and extracted with 5% NaHCO$_3$ and H$_2$O. The organic phase was dried with K$_2$CO$_3$, filtered, and concentrated under reduced pressure. Silica gel chromatography (CH$_2$Cl$_2$: MeOH:NH$_4$OH; 93:7:0.7) of the concentrate afforded II (9.02 g, 78.2%). Treatment of the base (1.0 g) with ethanolic HCl and crystallization from i-PrOH/EtOH yielded the hydrochloride salt of 11 (0.45 g, 32.1%, m.p. 191°–193° C.).

4-(5-Methoxy-4-pyrimidinyl)-2-methyl-piperazine—Method 2

A solution of 2-methylpiperazine (20 g) in water (100 mL) was reacted with solid 4,6-dichloro-5-methoxypyrimidine (5.00 g, 27.9 mmol) in a procedure similar to that given for Method 2 of Example 21. After hydrogenation and filtration of the catalyst, the product was extracted from the filtrate with CH$_2$Cl$_2$. The extracts were concentrated in vacuo, and the residue was Kügelrohr distilled to give a clear oil (5.46 g, 99.8%). The oil was dissolved in acetonitrile and concentrated HCl added to form the salt which was recrystallized from i-PrOH and dried in vacuo to give the product as a white powder (4.02 g, m.p. 185°–188° C.

B. Preparation of Formula I Products

Example 23

3-[3-[4-(5-Methoxy-4-pyrimidinyl)-2-methyl-1-piperazinyl]propyl]-5-fluoroindole

To a solution of 5-fluoro-3-(3-p-toluenesulfonyloxy-propyl)-indole (1.16 g, 3.34 mmol) in 50 mL of acetonitrile was added 1-(5-methoxy-4-pyrimidinyl)-2-methyl-piperazine(0.83 g, 4.0 mmol), KI (0.56 g, 4.0 mmol) and diisopropylethylamine (3.48 mL, 20.0 mmol) and the mixture was heated to reflux under Ar for 20 h. The resulting mixture was diluted with ethyl acetate, washed (H$_2$O, brine), dried (Na$_2$SO$_4$) and evaporated to give a foam. Flash chromatography (SiO$_2$/ethyl acetate-methanol=95:5) of this material gave the product (0.65 g, 46%) as a colorless foam: $^1$Hnmr (200 MHz, CDCl$_3$) δ 8.32 (s, 1H), 8.00 (br s, 1H), 7.88 (br s, 1H), 7.32–7.20 (m, 2H), 7.03 (d, J=1.7 Hz, 1H), 6.94 (dt, J=9.1, 2.3 Hz, 1H), 4.30–4.16 (m, 2H), 3.85 (s, 3H), 3.42–3.28 (m, 1H), 3.10–2.64 (m, 5H), 2.61–2.28 (m, 3H), 1.96–1.82 (m, 2H), 1.07 (d, J=6.2 Hz, 3H). The foam was taken up in ethanol and treated with excess ethanolic HCl to give a white precipitate. The solid was filtered and washed with ether to give 0.6 g of a white solid. Recrystallization from methanol-ether gave the hydrochloride (0.58 g) as fluffy white crystals: m.p. 204° C. (dec); IR (KBr) 3410, 1633, 1550 cm$^{-1}$; $^1$Hnmr (200 mHZ, d$_6$-DMSO) δ 11.62 (br s, 1H), 11.00 (br s, 1H), 8.64 (s, 1H), 8.20 (s, 1H), 7.35–7.29 (m, 3H), 6.90 (dt, J=9.3, 2.4 Hz, 1H), 4.92–4.78 (m, 2H), 3.90 (s, 3H), 3.85–3.04 (m, 9H), 2.81–2.69 (m, 2H), 2.07–2.02 (m, 2H), 1.36 (d, J=5.7 Hz, 3H).

Anal Calcd for C$_{21}$H$_{26}$FN$_5$O.1.85 HCl: C, 55.93; H, 6.23; N, 15.53; Found: C, 55.91; H, 6.48; N, 15.27.

Example 24

3-[3-[4-(5-Methoxy-4-pyrimidinyl)-1-piperazinl]-propyl]-5-fluoroindole

To a solution of 5-fluoro-3-(3-p toluenesulfonyloxy-propyl)-indole (1.16 g, 3.34 mmol) in 50 mL of acetonitrile was added 1-(5-methoxy-4-pyrimidinyl)piperazine (0.78 g, 4.0 mmol), KI (0.56 g, 4.0 mmol) and diisopropylethylamine (3.48 mL, 20.0 mmol) and the mixture was heated to reflux under Ar for 20 h. The resulting mixture was diluted with ethyl acetate, washed (H$_2$O, brine), dried (Na$_2$SO$_4$) and evaporated to give a gum. Flash chromatography (SiO$_2$/ethyl acetate-methanol=95:5) of this material gave a gum which was triturated with CH$_2$Cl$_2$-ether. Evaporation of the supernatant gave a foam which solidified upon the addition of ether. This solid was recrystallized from ethyl acetate-hexane to give the product (0.70 g, 57%) as off-white crystals: m.p. 119°-122° C.; IR (KBr) 3190, 15SO cm$^{-1}$; $^1$Hnmr (200 MHz, CDCl$_3$) δ 8.33 (s, 1H), 8.04 (br 2, 1H), 7.89 (s, 1H), 7.29-7.21 (m, 2H), 7.04 (d, J=2.2 Hz, 1H), 6.93 (dt, J=9.1, 2.4 Hz, 1H), 3.85 (s, 3H), 3.80 (t, J=5 Hz, 4H), 2.76 (t, J=7.5 Hz, 2H), 2.55 (t, J=5 Hz, 4H), 2.50-2.43 (m, 2H), 2.00-1.85 (m, 2H).

Anal. Calcd for C$_{20}$H$_{24}$FN$_5$O.0.5 H$_2$O; C, 63.47; H, 6.66; N, 18.51; Found: C, 63.89; H, 6.66; N, 18.55.

Example 25

3-[3-[4-(5-Methoxy-4-pyrimidinyl)-2-methyl-1-pioerazinyl]-propyl]-6-fluoroindole To a solution of 6-fluoro-3-(3-p-toluenesulfonyloxypropyl)-indole (0.87 g, 2.5 mmol) in 50 mL of acetonitrile was added 1-(5-methoxy-4-pyrimidinyl)-2-methyl-piperazine (0.68 g, 3.2 mmol), KI (0.45 g, 2.7 mmol) and diisopropylethylamine (3.5 mL, 20 mmol) and the mixture was diluted with ethyl acetate, washed (H$_2$O, brine, dried (Na$_2$SO$_4$) and evaporated to give a gum. Flash chromatography (SiO$_2$/ethyl acetate-methanol 95:5 - 50:50) gave the product (0.65 g, 6B%) as a gum: $^1$Hnmr (200 MHz, CDCl$_3$) δ 8.32 (s, 1H), 8.09 (br s, 1H), 7.87 (s, 1H), 7.49 (dd, J=8.7, 5.3 Hz, 1H), 7.02 (dd, J=9.7, 2.2 Hz, 1H), 6.96 (d, J=2 Hz, 1H), 6.92-6.82 (m, 1H), 4.30-4.14 (m, 2H), 3.84 (s, 3H), 3.42-3.29 (m, 1H), 3.06 (dd, J=12.8, 9.0 Hz, 1H), 2.96-2.34 (m, 7H), 1.97-1.86 (m, 2H), 1.07 (d, J=6.2 Hz, 3H).

The gum was taken up in excess ethanolic HCl and the solution was evaporated and the residue was triturated with ether to give a beige solid. This material was precipitated from ethanol with ether to give the hydrochloride (0.17 g) as a solid: m.p. 150° C. (dec); IR (KBr) 3418, 1620, 1548 cm$^{-1}$; $^1$Hnmr (200 MHz, d$_6$-DMSO) δ 11.4 (br s, 1H), 10.96 (s, 1H), 8.60 (s, 1H), 8.19 (s, 1H, 7.53 (dd, J=8.6, 5.5 Hz, 1H), 7.20 (s, 1H), 7.10 (dd, J=10.2, 2.2 Hz, 1H), 6.89-6.78 (m, 1H), 4.86-4.74 (m, 2H), 3.90 (s, 3H), 3.82-3.05 (m, 7H), 2.8-2.7 (m, 2H), 2.1-2.0 (m, 2H), 1.35 (d, J=5.3 Hz, -2H), 1.17 (d, J=6.0 Hz, 1H).

Anal. Calcd for C$_{21}$H$_{26}$FN$_5$O.2HCl.2H$_2$O: C, 51.22; H, 6.55; N, 14.22; Found: C, 51.46; H, 6.42; N, 13.93.

Example 26

3-3-[4-(5-Methoxy-4-pyrimidinyl)-2-methyl-piperazinyl]-propyl]-1-methylindole

To a solution of 1-methyl-3-(3-p-toluenesulfonyloxypropyl)-indole (0.75 g, 2.2 mmol) in 50 mL of acetonitrile was added 1-(5-methoxy-4-pyrimidinyl)-2-methylpiperazine (0.54 g, 2.6 mmol), KI (0.37 g, 2.2 mmol) and diisopropylethylamine (3.5 mL, 20 mmol) and the mixture was heated to reflux under Ar for 20 h. The resulting mixture was diluted with ethyl acetate, washed (H$_2$O, brine, dried (Na$_2$SO$_4$) and evaporated to give a foam. Flash chromatography (SiO$_2$/ethyl acetatemethanol=98:2) of this material gave the product (0.48 g, 48%) as an oil: $^1$Hnmr (200 MHz, CDCl$_3$) δ 8.32 (s, 1H), 7.88 (s, 1H), 7.58 (d, J=7.8 Hz, 1H), 7.31-7.05 (m, 3H), 4.30-4.14 (m, 2H), 3.85 (s, 3H), 3.74 (s, 3H), 3.42-2.39 (m, 9H), 1.99-184 (m, 2H), 1.10 (d, J=6.2 Hz, 3H), 2.96-2.34 (m, 7H), 1.97-1.86 (m, 2H), 1.07 (d, J=6.2 Hz, 3H).

This material was taken up in ether and the solution was treated with excess ethanolic HCl. The resulting precipitate was filtered and dried to give a solid which was crystallized from methanol-ether to afford the hydrochloride (0.40 g) as a an off-white solid: m.p. 210° C. (dec); IR (KBr) 1630, 1547 cm$^{-1}$; $^1$Hnmr (200 MHz, d$_6$-DMSO) δ 11.03 (br s, 1H), 8.53 (s, 1H), 8.18 (s, 1H), 7.56 (d, J=7.7 Hz, 1H), 7.38 (d, J=8.0 Hz, 1H), 7.17-6.98 (m, 3H), 4.78-4.67 (m, 2H), 3.89 (s, 3H), 3.73 (s, 3H), 3.6-3.0 (m, 8H), 2.8-2.7 (m, 2H) 2.2-2.0 (m, 1H), 1.35 (d, J=4.7 Hz, 2H), 1.18 (d, J=5.7 Hz, 1H).

Anal. Calcd for C$_{22}$H$_{29}$N$_5$O.2HCl: C, 58.40; H, 6.91; N, 15.48; Found: C, 58.37; H, 6.85; N, 15.3.

Using modifications of the foregoing procedures, additional Formula I products may be obtained.

TABLE 1

Formula I Compounds

| Ex. No. | R$^1$ | R$^2$ | R$^3$ | R$^4$ | R$^5$ | R$^6$ | n | % Yield | MP (°C.) |
|---|---|---|---|---|---|---|---|---|---|
| 27 | H | H | H | H | H | 5-EtO | 3 | 99 | >230 |
| 28 | H | H | H | H | H | 5-MeO | 3 | 58 | 221-224 |
| 29 | H | H | H | 5-Cl | H | 5-MeO | 3 | 46 | 200-203 |
| 30 | H | H | 6-F | 5-F | Me | 5-MeO | 3 | 44 | 127-129 |
| 31 | H | H | H | 5-F | H | 5-MeO | 2 | 85 | 158-160 |
| 32 | H | H | H | 5-Cl | Me | 5-MeO | 3 | 45 | 169 |
| 33 | H | H | H | H | Et | 5-MeO | 3 | 72 | 210 |
| 34 | H | H | 6-F | 5-F | H | 5-MeO | 2 | 74 | 102-104 |
| 35 | H | H | H | 5-F | Me | 5-MeO | 2 | 34 | 192-194 |
| 36 | Me | H | H | H | Me | 5-MeO | 3 | 48 | 210 |
| 37 | H | H | H | H | H | 6-MeO | 3 | 52 | 131-133 |
| 38 | H | H | H | H | Me | 5-EtO | 3 | 53 | >230 |
| 39 | H | H | H | H | Me | 6-MeO | 3 | 38 | 160 |

BIOLOGICAL ACTIVITIES OF FORMULA I COMPOUNDS INHIBITION OF SEROTONIN UPTAKE (IN VITRO)

| Ex. No. | IC$_{50}$(nM) |
|---|---|
| 23 | 0.03 |
| 24 | 0.3 |
| 25 | 3.7 |
| 27 | 6.35 |
| 28 | 4.3 |
| 29 | 2.9 |
| 30 | 1.46 |
| 31 | 0.92 |
| 32 | 2.1 |
| 33 | 2.64 |
| 34 | 3.1 |
| 35 | 3.1 |
| 36 | 4.7 |
| 37 | 5.85 |
| 38 | 13.4 |
| 39 | 9.3 |

We claim:

1. A compound of Formula I or a pharmaceutically acceptable acid addition salt thereof

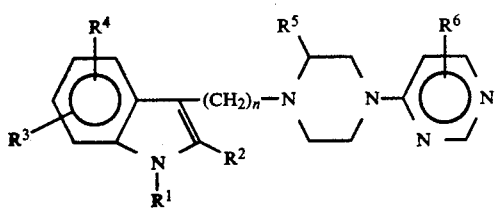

wherein $R^1$ is selected from hydrogen, lower alkyl and lower alkyl meaning $C_{1-4}$;

$R^2$ and $R^5$ are independently selected from hydrogen and lower alkyl;

$R^3$ and $R^4$ are independently selected from hydrogen, lower alkyl, lower alkoxy, lower alkylthio, carboxamide, halogen and trifluoromethyl;

$R^6$ is lower alkoxy; and n is the integer 2 or 3.

2. The compound of claim 1 wherein $R^4$ is 5-fluoro.

3. The compound of claim 1 wherein $R^6$ is 5-methoxy.

4. The compound of claim 1, 1-[3-(1H-indol-3-yl)propyl]-4-[5-methoxy-4-pyrimidinyl)piperazine.

5. The compound of claim 1, 1-[2-(5-fluoro-1H-indol-3-yl)ethyl]-4-(5-methoxy-4-pyrimidinyl)piperazine.

6. The compound of claim 1, 1-[2-(5-fluoro-1H-indol-3-yl)ethyl]-4-(5-methoxy-4-pyrimidinyl)-2-methylpiperazine.

7. The compound of claim 1, 1-[3-(5-fluoro-1H-indol-3-yl)propyl]-4-(5-methoxy-4-pyrimidinyl)-2-methylpiperazine.

8. The compound of claim 1, 1-[3-(5-fluoro-1H-indol-3-yl)propyl]-4-(5-methoxy-4-pyrimidinyl)piperazine.

9. The compound of claim 1, 4-(5-methoxy-4-pyrimidinyl)-1-[3-(1-methyl-1H-indol-3-yl)propyl]-2-methylpiperazine.

10. The compound of claim 1, 1-[3-(6-fluoro-1H-indol-3-yl)propyl]-4-(5-methoxy-4-pyrimidinyl)-2-methylpiperazine.

11. The compound of claim 1, 1-[3-(5-chloro-1H-indol-3-yl)propyl]-4-(5-methoxy-4-pyrimidinyl)-2-methylpiperazine.

12. The compound of claim 1, 1-[3-(1H-indol-3-yl)propyl]-4-(6-methoxy-4-pyrimidinyl)piperazine.

13. The compound of claim 1, 1-[3-(1H-indol-3-yl)propyl]-4-(6-methoxy-4-pyrimidinyl)-2-methylpiperazine.

14. The compound of claim 1, 1-[3-(5-chloro-1H-indol-3-yl)propyl]-4-(5-methoxy-4-pyrimidinyl)piperazine.

15. The compound of claim 1, 1-[3-(5,6-difluoro-1H-indol-3-yl)propyl]-4-(5-methoxy-4-pyrimidinyl)-2-methylpiperazine.

16. The compound of claim 1, 1-[3-(5,6-difluoro-1H-indol-3-yl)propyl]-4-(5-methoxy-4-pyrimidinyl)piperazine.

17. The compound of claim 1, 2-ethyl-1-[3-(1H-indol-3-yl)propyl]-4-(5-methoxy-4-pyrimidinyl)piperazine.

18. The compound of claim 1, 4-[5-ethoxy-4-pyrimidinyl)-1-[3-(1H-indol-3-yl)propyl]piperazine.

19. The compound of claim 1, 4-[5-ethoxy-4-pyrimidinyl)-1-[3-(1H-indol-3-yl)propyl]-2-methylpiperazine.

20. A method for ameliorating a state of depression in a mammal comprising administration to the mammal of an effective antidepressant amount of a compound claimed in claim 1.

21. A pharmaceutical composition in unit dosage form suitable for systemic administration to a mammalian host comprising a pharmaceutical carrier and from about 1 to 500 mg of an antidepressant compound selected from the compounds claimed in claim 1.

* * * * *